United States Patent [19]

Seifert et al.

[11] Patent Number: 4,922,008
[45] Date of Patent: May 1, 1990

[54] PROCESS FOR THE PRODUCTION OF 4-NITROTOLUENE-2-SULFONIC ACID

[75] Inventors: Gottfried Seifert; Sebastian Stäubli, both of Magden, Switzerland; Josef H. Wieland, Bad Säckingen, Fed. Rep. of Germany; Willy Regenass, Muttenz; Martin Buerli, Magden, both of Switzerland; John G. Lee, Saraland; Richard B. Lund, Jackson, both of Ala.

[73] Assignee: Ciba-Geigy Corporation, Ardsley, N.Y.

[21] Appl. No.: 45,734

[22] Filed: Apr. 29, 1987

Related U.S. Application Data

[63] Continuation of Ser. No. 807,387, Dec. 10, 1985, abandoned, which is a continuation-in-part of Ser. No. 672,034, Nov. 16, 1984, abandoned.

[30] Foreign Application Priority Data

Nov. 28, 1983 [CH] Switzerland .......................... 6350/83

[51] Int. Cl.$^5$ ............................................. C07C 143/24
[52] U.S. Cl. ........................................ 562/58; 562/60
[58] Field of Search ................ 260/505 R; 562/58, 60

[56] References Cited

U.S. PATENT DOCUMENTS 3,840,591 10/1974 Lee et al. .
3,923,666 12/1975 Dill .
3,935,237 1/1976 Davidsohn .
3,941,810 3/1976 Koebner .
3,946,037 3/1976 Koebner .
4,382,039 5/1983 Goldschmitt ...................... 260/505

FOREIGN PATENT DOCUMENTS 1164752 9/1969 United Kingdom .
1569061 6/1980 United Kingdom .

OTHER PUBLICATIONS

Gilbert, Sulfonation & Related Reactions (1965) p. 82.
Chemical Abstracts 9394991u, (1980) p. 616.
CA 9371290a, (1980) p. 931 25–Noncondensed Aromatics.

Primary Examiner—B. Alan Siegel
Attorney, Agent, or Firm—Kevin T. Mansfield

[57] ABSTRACT

A process for the preparation of 4-nitrotoluene-2-sulfonic acid by sulfonating 4-nitrotoluene with oleum or liquid $SO_3$ is described. The sulfonation is carried out continuously with oleum of at least 50% concentration or liquid 100% $SO_3$ while keeping the conversion of 4-nitro-toluene in the reaction mixture at $\geq 90\%$ during the entire reaction course.

The process is inherently non-polluting, and provides the product in high yield and low sulfuric acid content in a form usable for 4,4'-dinitrostilbene-2,2'-disulfonic acid production without further purification.

15 Claims, No Drawings

PROCESS FOR THE PRODUCTION OF 4-NITROTOLUENE-2-SULFONIC ACID

CROSS REFERENCE TO RELATED APPLICATION

This application is a continuation now abandoned of application Ser. No. 807,387, filed 12/10/85, which is a continuation-in-part of Applicant applications Ser. No. 672,034 now abandoned, filed Nov. 16, 1984.

The present invention relates to a process for the preparation of 4-nitrotoluene-2-sulfonic acid by sulfonating 4-nitrotoluene with high strength oleum or liquid 100% $SO_3$.

4-Nitrotoluene-2-sulfonic acid is an important intermediate for the production of fluorescent whitening agents, thousands of tons of which are manufactured annually. It is used principally as starting material for the production of 4,4'-dinitrostilbene-2,2'-disulfonic acid, which in turn is used for the manufacture of a host of fluorescent whitening agents, based on cyanuric chloride, of the 4,4'-bis([1,3,5-triazin-2-yl]amino)-stilbene-2,2'-disulfonic acid type. Further substantial amounts of 4-nitrotoluene-2-sulfonic acid are required for the synthesis of fluorescent whitening agents with other basic structures and of various dyes.

The large-scale production of 4-nitrotoluene-2-sulfonic acid has up to now been carried out almost exclusively by sulfonating 4-nitrotoluene with 20-25% oleum. This process, however, results in the formation of large amounts of waste sulfuric acid, which is undesirable for environmental reasons. Further, the regeneration or elimination of the acid mother liquors is a technical problem and also makes the process uneconomical. There has therefore been no lack of attempts to overcome the drawbacks of this sulfonation process. In particular, attempts have been made to sulfonate 4-nitrotoluene directly with $SO_3$.

A process for the preparation of 4-nitrotoluene-2-sulfonic acid is described in U.S. patent specification 3,840,591, wherein molten 4-nitrotoluene is sulfonated directly with a mixture of $SO_3$, and an inert gas. This process, however, gives rise to the formation of complex colored compounds which accumulate in the final product. The dark product must therefore be subjected to fairly elaborate purification operations. In addition, the need to mix the gaseous $SO_3$ with an inert gas necessitates a gas scrubbing facility to remove small amounts of pollutants contained in the gas before it is vented to the atmosphere. As an alternative, the inert gas may be recycled but this requires mechanical means for controlling the recycling of the gas through the system as well as some means for accurately controlling the ratio of $SO_3$ fed to the recycled inert gas. Either alternative requires an investment in essentially non-productive equipment and all of the expenses such as labor energy, maintenance and downtime associated with the operation of this equipment. Either alternative makes the process more complex than is desirable.

A process for the preparation of aromatic sulfonic acids by treating aromatic hydrocarbons with gaseous $SO_3$ is described in DE-A 2,353,918 and DE-A 2,354,097. In this process the reaction takes place under reflux conditions while constantly maintaining a substantial excess of aromatic hydrocarbon as heat transfer medium. In DE-A 2 354 097, an inert compound which dissolves the aromatic substance and the sulfonic acid formed therefore is used as heat transfer medium. The reaction temperature, which is regulated via the pressure, is in the range from 20° to 100° C. and accords with the reflux temperature.

According to the above described process, physical factors make it possible to carry out the sulfonation of 4-nitrotoluene (boiling point: 105° C./12 mbar) without a solvent technically only with considerable effort. Even the proposed use of solvents involves an additional complication, provided organic solvents which are sufficiently stable to $SO_3$ are available at all in the indicated temperature range.

The preparation of 4-nitrotoluene-2-sulfonic acid is taught in Example 2 of French patent specification 1,555,394, wherein gaseous $SO_3$ is bubbled into molten 4-nitrotoluene at 80°-90° C. The temperature is then increased to 115°-120° C. and kept for 8 hours. The hot melt is discharged into water to give a dark brown solution of 4-nitrotoluene-2-sulfonic acid. According to Swiss patent specification 478 772, column 2, paragraph 3, the sulfonation can also be carried out without solvents by bubbling gaseous sulfur trioxide which is strongly diluted with an inert gas such as nitrogen, or oxidized residual gases from e.g. a contact sulfuric acid plant, into the liquid or molten nitroaromatic compounds.

The sulfonation of molten 4-nitrotoluene with pure gaseous $SO_3$ (such a sulfonation is described e.g. in DE-A 2,837,549) is, for practical purposes not suitable, as the high melting point of 4-nitrotoluene-2-sulfonic acid would make it necessary to raise the sulfonation temperature to its decomposition range.

If the sulfonation with gaseous $SO_3$ is not carried out to complete conversion of 4-nitrotoluene, it is possible to keep the reaction temperature fairly low (q.v. EP-A 18541). However, the drawback is here that it is necessary to extract unreacted 4-nitrotoluene with solvents from the sulfonation mixture. If it is desired to avoid a loss in yield, the 4-nitrotoluene must be isolated from the extract and recycled to the reaction. All this complicates the process.

The process described in EP-A 83555 attempts to avoid the drawback referred to above by adding a small amount of sulfuric acid before the sulfonation. However, as in all processes carried out with gaseous $SO_3$, the handling of the latter presents certain difficulties and involves the use of more apparatus. If the $SO_3$ is obtained e.g. from 65% oleum, this means an additional process step compared with the direct sulfonation with oleum.

A number of other sulfonation processes using $SO_3$ are known in which the $SO_3$ is diluted with an inert gas in order to keep the exothermic reaction under control and to avoid the problem of the formation of by-products, especially of sulfones (these problems arise in the sulfonation using pure $SO_3$). Reference is made in this connection e.g. to DE-A 2,800,788, DE-A 2,413,444 and JP-A 55-4357. The drawback of these procedures generally is that substantial amounts of inert gas are required and that the waste gas of $SO_3$ or the sulfuric acid formed as a result of the admission of moisture, as well as of entrained hydrocarbon, has to be purified. This too is highly uneconomical and undesirable.

A drastic reduction in the amount of waste sulfuric acid in the standard process described at the outset (sulfonation of 4-nitrotoluene with 20-25% oleum) could in principle be achieved by increasing the concentration of SO₃ in the oleum, for example by using commercially available 65% oleum. However, it is known that the sulfonation of aromatic hydrocarbons with oleum results increasingly in the occurrence of side reactions as soon as the SO₃ concentration in the oleum is raised. These side reactions lead to a black discoloration of the sulfonation products and thus also to reductions in yield. These side reactions increase with increasing temperature. This problem arises in particular in the sulfonation of 4-nitrotoluene, as the sulfonation must be carried out at fairly high temperature. For this reason it has so far not been possible to find an economical and technically useful process for sulfonating 4-nitrotoluene with oleum in which the concentration of SO₃ is more than 30%.

Surprisingly, it has now been found that it is also possible to sulfonate 4-nitrotoluene with more than 50% oleum readily and in high yield and to obtain sufficiently pure 4-nitrotoluene-2-sulfonic acid by carrying out the sulfonation continuously in a reaction mixture in which the conversion of 4-nitrotoluene is $\geq 90\%$.

Accordingly, the process of the present invention for the preparation of 4-nitrotoluene-2-sulfonic acid by sulfonating 4-nitrotoluene comprises carrying out the sulfonation continuously with at least 50% oleum or pure liquid SO₃ while keeping the conversion of 4-nitrotoluene in the reaction mixture, to which 4-nitrotoluene and oleum are added, at >90% during the entire course of the reaction.

It is preferred to introduce both the 4-nitrotoluene and the oleum or liquid SO₃ separately below the surface of the molten 4-nitrotoluene-2-sulfonic acid.

The residence time which is necessary to achieve and maintain an at least 90% conversion of 4-nitrotoluene in the reaction vessel (or in the first reaction vessel, if several are employed) can vary within wide limits and depends on the reaction temperature and on the amount of SO₃ added as oleum or liquid SO₃. It is advantageous to carry out the reaction in the temperature range from 80° to 140° C., preferably from 110° to 120° C. The corresponding parameters (rate of addition of 4-nitrotoluene and oleum, temperature, residence time) are determined in preliminary experiments. It is expedient to verify over the entire reaction course whether the at least 90% conversion of 4-nitrotoluene is being kept. For example, a sample is taken from the reaction mixture at specific intervals and the amount of reacted 4-nitrotoluene therein is determined analytically. If necessary, one or more of the above mentioned parameters can be readjusted. In the preferred temperature range the reaction is completed in about 2-3 hours depending on the SO₃ excess.

It is preferred to use 1.0 to 1.5 moles of SO₃ in the form of oleum per mole of 4-nitrotoluene. A slight stoichiometric excess of SO₃, e.g. 1.05 to 1.1 moles per mole of nitrotoluene, has proved particularly advantageous.

The sulfonating agent employed is oleum of at least 50% strength or liquid SO₃. For example, 60-70%, preferably 65% oleum (=65% of SO₃), which is commercially available, can be advantageously used. However, the process can also very conveniently be carried out with oleum of higher concentration, for example with 70-85% oleum such as 81% or 85% oleum. The process can also be carried out with pure liquid SO₃.

The process of this invention can be carried out in all equipment and apparatus suitable for continuous reactions known in chemical process engineering. Suitable for carrying out the process is a stirred flow reactor, especially a cascade of agitated vessels. The process of the invention can also be carried out in a recycling apparatus, for example a loop reactor. If desired, it is also possible to provide additional reactors, for example residence time vessels, a tubular reactor or a cascade of agitated vessels.

It is particularly preferred to carry out the reaction in a cascade of agitated vessels comprising a main reactor and reaction vessels for further reactions.

To avoid the formation of byproducts (black dicoloration) from the reaction of 4-nitrotoluene and the concentrated oleum on first initiating the reaction, it is possible to charge the (first) reactor with a sulfonation batch in which the conversion of 4-nitrotoluene is at least 90% (e.g. a fully reacted sulfonation batch) and then to add 4-nitrotoluene and oleum.

However, it is also possible to charge the reactor with concentrated sulfuric acid and then to add -nitrotoluene and oleum simultaneously, thereby avoiding the formation of byproducts (black discoloration) caused by the initial dilution of oleum. A 4-nitrotoluene conversion of $\geq 90\%$ takes place very rapidly in the reaction mixture containing an excess of sulfuric acid, whereby the necessary condition of the process is fulfilled.

The process of this invention while primarily directed to continuous practice may also be batch operated. A heel of the 4-nitrotoluene-2-sulfonic acid from a previous batch is kept in the reactor. The nitrotoluene PNT conversion in this heel is 90-100% (usually about 99%). The heel is heated to 90°-100° C., and 4-nitrotoluene and high strength oleum or liquid SO₃ are fed simultaneously until the reactor is substantially full. The reactant feeds are at a rate to ensure that the reaction medium contains at least about 90% 4-nitrotoluene-2-sulfonic acid.

The feeds are terminated and the reaction temperature maintained above 100° C. but below about 140° C. until substantial completion. The reaction mass (less retained heel) is then discharged and a new batch is started.

Depending on the envisaged further use, the working up of the reaction mixture can be effected by different methods. The process of this invention affords 4-nitrotoluene-2-sulfonic acid in good (98-99.5%) yield, high purity (few byproducts, e.g. 2,2'-dimethyl-5,5'-dinitrodiphenylsulfone) and acceptable color. The reaction mixture can therefore be further processed directly, for example for the preparation of 4,4'-dinitrostilbene-2,2'-disulfonic acid. Most conveniently it can be diluted with water to e.g. a 30-35% concentration of 4-nitrotoluene-2-sulfonic acid and then used for the preparation of 4,4'-dinitrostilbene-2,2'-disulfonic acid. If the presence of sulfuric acid in the reaction mixture interferes with the further processing, the 4-nitrotoluene-2-sulfonic acid can also be isolated.

Since use of high strength oleum leads to less sulfuric acid in the reaction mixture, use of oleum concentrations above 70% are especially desirable if the product is to be used directly. A stable 80% oleum is now available and, in addition to liquid SO₃, is a preferred sulfonation agent.

Where isolation is desired, it is conveniently effected by diluting the sulfonation mixture to a 60-75% concentration of sulfuric acid, preferably to a concentration of about 70%, and to a 30-40% concentration of 4-nitrotoluene-2-sulfonic acid, preferably to a concentration of about 35%. The 4-nitrotoluene-2-sulfonic acid crystallizes out during this dilution and can be isolated in conventional manner. The dilution to the appropriate concentration of sulfuric acid and 4-nitrotoluene-2-sulfonic acid can be made with water. However, to keep the amount of waste sulfuric acid low, it is preferred to make the dilution with water and mother liquor from previous crystallization steps (recycling the mother Liquor which contains sulfuric acid). This can be done for example by diluting the reaction mixture first with water to the desired sulfuric acid concentration indicated above, and then with mother liquor from a previous crystallization step to the desired concentration of 4-nitrotoluene-2-sulfonic acid. It is also possible, however, to add the reaction mixture to the calculated amount of water and mother liquor, affording the desired concentration of sulfuric acid and 4-nitrotoluene-2-sulfonic acid, which latter crystallizes out.

In the course of diluting and cooling the sulfonation mixture, any 4-nitrotoluene-2-sulfonic anhydride which may have formed is almost immediately converted to the free acid. This reaction takes place readily at temperatures above about 80° C.

The resultant product is very pure and can be further used without additional purification. A separation of sulfone is not necessary, as only very insignificant amounts are present.

As mentioned at the outset, the bulk of the 4-nitrotoluene-2-sulfonic acid obtained is used for the preparation of 4,4'-dinitrostilbene-2,2'-disulfonic acid. This is accomplished by reacting for example an aqueous solution of 4-nitrotoluene-2-sulfonic acid (app. 30-40%) with an oxidizing agent (e.g. atmospheric oxygen, hypochlorite etc.). The resultant 4,4'-dinitrostilbene-2,2'-disulfonic acid can then be reduced to 4,4'-diaminostilbene-2,2'-disulfonic acid (q.v. for example Ber. 30, 3100; EP-A 83555, pp. 11/12, 15/16), which is an important intermediate for the manufacture of fluorescent whitening agents (q.v. for example Angew. Chem. 87, 693 (1975)].

Particularly preferred embodiments of the process of the invention are described in the following Examples, but without any limitation being implied. Unless otherwise indicated, parts and percentages are by weight.

EXAMPLE 1

The first agitated vessel of a cascade of 4 agitated vessels with respective volumes of 800 ml, 400 ml, 400 ml and 400 ml is initially charged at 115° C. with 200 g of 100% sulfuric acid and then 600 g (4.376 moles) of 4-nitrotoluene and 566 g of 65% oleum (4.595 moles of $SO_3$) are simultaneously added continuously per hour. The conversion of 4-nitrotoluene in the first agitated vessel is 93% in stationary operation. The complete conversion of 4-nitrotoluene to 4-nitrotoluene-2-sulfonic acid takes place at 115° C. in the successive agitated vessels. The residence time in the cascade is 2½ hours.

To isolate the 4-nitrotoluene-2-sulfonic acid, the sulfonation mixture is adjusted to a sulfuric acid concentration of 70% and diluted with mother liquor from a previous crystallization to a 4-nitrotoluene-2-sulfonic acid concentration of 35%. After centrifuging at room temperature, 936 g of 100% 4-nitrotoluene-2-sulfonic acid (98.5% of theory) are obtained from 600.0 g of 4-nitrotoluene.

It is also possible to charge the first agitated vessel with a corresponding amount of a fully reacted sulfonation batch from a previous production phase instead of with 200 g of 100% sulfuric acid.

EXAMPLE 2

The cascade of agitator vessels described in Example 1 is employed. The first vessel is charged with 200 g of 100% sulfuric acid and then 600 g (4.376 moles) of 4-nitrotoluene and 454 g of 85% oleum (4.814 moles of $SO_3$) are simultaneously added continuously per hour at 115° C. The 85% oleum is prepared by mixing 65% oleum and 100% $SO_3$ and adding it from a pressure vessel at 50° C. The conversion of 4-nitrotoluene in the first agitator vessel is 92% in stationary operation. The residue time in the cascade is 170 minutes. The sulfonation mixture is diluted with water to a 4-nitrotoluene-2-sulfonic acid concentration of 35%. In stationary operation, about 2690 g of 4-nitrotoluene-2-sulfonic acid having a concentration of 35% is obtained from 600 g of 4-nitrotoluene by adding 1635 g of water. This corresponds to 941 g of 100% 4-nitrotoluene-2-sulfonic acid or 99.0% of theory (based on 4-nitrotoluene).

The 4-nitrotoluene-2-sulfonic acid solution with a sulfuric acid concentration of about 4% is used directly for further processing (preparation of 4,4'-dinitrostilbene-2,2'-disulfonic acid).

EXAMPLE 3

The 1000 ml initial reactor vessel of a cascade of 4 agitated vessels was provided with an overflow arm at about the 500 ml level, leading to the first subsequent stage of the cascade system. The initial reactor vessel is provided with feed orifices for introducing 4-nitrotoluene and oleum at levels proximate to the bottom of the vessel. The reactor contained approximately 500 ml of 4-nitrotoluene-2-sulfonic acid reaction mass from a previous run and was heated to about 100° C. The flow of 80% oleum (83.27%) and PNT was begun at a rate of 3.49 g/min and 4.103 g/min respectively. After about 15 minutes, overflow started to the second stage reactor (275 ml overflow level) in the cascade system. After an additional 10 to 15 minutes, the second stage reactor overflowed to the third stage ( 250 ml overflow level). After about 15 minutes, the second stage reactor overflowed to the fourth stage vessel ( 500 ml overflow level) which had been previously filled with water. Once overflow was established from the third stage reactor to the fourth stage reactor, which was held at 80°-90° C., a flow of water to the dilution vessel was started at 14.5 g/min. This water flow served to dilute the 4-nitrotoluene-2-sulfonic acid in the sulfonation mass and to hydrolyze any anhydride present to the free acid for a final 4-nitrotoluene-2-sulfonic acid concentration of about 30%. After 2.7 hours of operation, the first three cascade reactors containing the molten sulfonation mass were sampled. Conversion of 4-nitrotoluene in the first, second, and third cascade vessels was 98.4%, 99.3%, and 99.99% respectively. A sample collected from the fourth reactor overflow for a 76 minute period, showed 4-nitrotoluene conversion to be 99.9% and 4-nitrotoluene- 2-sulfonic acid yield to be 99.2% with only 0.8% yield lost to sulfone formation. The final solution contained only 0.02% unreacted 4-nitrotoluene and about 16% sulfuric acid relative to 4-nitrotoluene-2-sulfonic acid.

After 2.8 hours of operation, the cascade reaction train was shut down, including 4-nitrotoluene, oleum, and water flows. The molten sulfonation mass in the first three reactors was allowed to solidify. Several days later, the reactors were heated to about 105°-115° C. The reactant feeds were restarted using oleum with an 82.7% free $SO_3$ assay. The 4-nitrotoluene and oleum flows were set at 4.18 g/min and 3.4 g/min ($SO_3$ excess 15%). The water flow to the fourth cascade vessel was started at 13.9 g/min. After operating the systems for five hours, samples were taken from the first three reactors and analyzed. The conversion in R-1, R-2 and R-3 were 97.0, 99.4, and 99.98 respectively. After 5.8 hours running, samples were again taken and analyzed. Conversion was 97.4% in the first reactor, 99.4% in the second and 100% in the third. The final sample collected at the overflow from the dilution vessel (#4) for 68 minutes showed 4-nitrotoluene conversion to be 99.7% with a yield of 99.15% of 4-nitrotoluene-2-sulfonic acid. 0.73% of theory yield was lost to sulfone formation. The final solution contained only 0.02% of unreacted 4-nitrotoluene and 16% sulfuric acid relative to 4-nitrotoluene-2-sulfonic acid. The dilute 30% 4-nitrotoluene-2-sulfonic acid solution is ready for use in other processes without any further treatment.

The cascade system contents were melted and feeds restarted using liquid $SO_3$ as the sulfonating agent. The conversions and yields after stabilization from the residues of previous runs shows 99 +% 4-nitrotoluene conversion and 97 +% 4-nitrotoluene-2-sulfonic acid yield. About 1.5% theory yield is lost to sulfone formation. The color of the samples was slightly darker but still within acceptable standards. No charring was noted and both 4-nitrotoluene-2-sulfonic acid yield and conversion were high, and the sulfonation mass flowed and was easily handleable at 115°–120° C.

EXAMPLE 4

The cascade reactor train was set-up as in Example 3 and was empty. Since the process cannot be started with 80% oleum it is started in the following manner. 290.0 g of 30% oleum (32.0%) was charged to the first reactor and heated to 80°–100° C. The heat is turned off and the 4-nitrotoluene feed is started at 3.89 g/min. After 33 minutes, about 80% of the stoichiometric amount of 4-nitrotoluene has been added to the first reactor which now contains about 40% 4-nitrotoluene-2-sulfonic acid, 60% sulfuric acid, and a small amount of free $SO_3$. The 80% oleum (82.9%) is now started at 3.24 g/min (about 18% $SO_3$ excess). The first reactor is kept at 115° C. and the system is operated continuously as in Example 3.

What is claimed is:

1. A process for the preparation of 4-nitrotoluene-2-sulfonic acid by sulfonating 4-nitrotoluene, which comprises carrying out the sulfonation continuously with oleum of 50–85% $SO_3$ content while maintaining the conversion in the reaction mixture, to which 4-nitrotoluene and said sulfonation source are added, at $\geq 90\%$ during the entire reaction course.

2. A process of claim 1, which comprises charging a reactor with a fully reacted sulfonation batch, heating said sulfonation batch until it is melted and then initiating the continuous reaction by adding 4-nitrotoluene and oleum to said reactor.

3. A process of claim 1, which comprises charging a reactor first with concentrated sulfuric acid to initiate the continuous reaction and then simultaneously adding 4-nitrotoluene and oleum to said reactor.

4. A process of claim 1, wherein the sulfonation is carried out in the temperature range from 80° to 140° C.

5. A process of claim 4, wherein the sulfonation is carried out in the temperature range from 110° to 120° C.

6. A process of claim 1, wherein the sulfonation reagent is 65% oleum.

7. A process of claim 1, wherein the sulfonation reagent is 80% oleum.

8. A process of claim 1, wherein 1.0 to 1.5 moles of $SO_3$ in the form of oleum are used per mole of 4-nitrotoluene.

9. A process of claim 1, wherein the sulfonation is carried out in a stirred flow reactor.

10. A process of claim 9, wherein the conversion of 4-nitrotoluene in the stirred flow reactor is adjusted to $\geq 90\%$ and 4-nitrotoluene and oleum are continuously added.

11. A process of claim 9, wherein the reaction is completed in a connected cascade of agitated vessels.

12. A process of claim 9, wherein the reaction is completed in a tubular reactor.

13. A process of claim 1, wherein the sulfonation is carried out in a loop reactor.

14. A process of claim 1, wherein the 4-nitrotoluene-2-sulfonic acid is isolated from the reaction mixture by diluting the reacting mixture with water and mother liquor from a previous 4-nitrotoluene-2-sulfonic acid crystallization step and adjusting it to a sulfuric acid concentration of 60–75% and to a 4-nitrotoluene-2-sulfonic acid concentration of 30–40% and separating the crystallized 4-nitrotoluene-2-sulfonic acid.

15. A process of claim 1, which comprises reacting the sulfonation batch further, with or without prior ilution with water, directly to 4,4'-dinitrostilbene-2,2'-disulfonic acid without further purification.

* * * * *